US006482651B1

(12) United States Patent
Smith et al.

(10) Patent No.: US 6,482,651 B1
(45) Date of Patent: Nov. 19, 2002

(54) AROMATIC ESTERS FOR MARKING OR TAGGING PETROLEUM PRODUCTS

(75) Inventors: Michael J. Smith, Newtown, PA (US); Bharat Desai, Ringwood, NJ (US)

(73) Assignee: United Color Manufacturing, Inc., Newtown, PA (US)

( * ) Notice: Subject to any disclaimer, the term of this patent is extended or adjusted under 35 U.S.C. 154(b) by 0 days.

(21) Appl. No.: 09/343,467

(22) Filed: Jun. 30, 1999

(51) Int. Cl.$^7$ ............................................. G01N 37/00
(52) U.S. Cl. ............................ 436/56; 436/60; 436/166
(58) Field of Search ........................... 436/800, 50, 60, 436/56, 164, 166; 252/510

(56) References Cited

U.S. PATENT DOCUMENTS

| | | | |
|---|---|---|---|
| 1,997,670 A | 4/1935 | Armour | |
| 2,046,365 A | 7/1936 | Cassidy et al. | |
| 2,063,575 A | 12/1936 | Adams | |
| 2,522,939 A | 9/1950 | Gamrath | |
| 2,522,940 A | 9/1950 | Gamrath | |
| 3,468,640 A | 9/1969 | Barusch et al. | 44/75 |
| 3,488,727 A | 1/1970 | Diassi et al. | 260/239.55 |
| 3,868,534 A | * 2/1975 | Pighin et al. | 313/358 |
| 3,883,568 A | 5/1975 | Turner et al. | 260/383 |
| 4,209,302 A | 6/1980 | Orelup | 44/59 |
| 4,288,402 A | 9/1981 | Ellis | 422/61 |
| 4,514,503 A | 4/1985 | Orelup | 436/60 |
| 4,613,878 A | * 9/1986 | Inaba et al. | 427/151 |
| 4,735,631 A | 4/1988 | Orelup | 44/59 |
| 4,764,290 A | 8/1988 | Currey | 252/11 |
| 4,764,474 A | 8/1988 | Orelup | 436/111 |
| 4,787,916 A | 11/1988 | Feldman | 44/92 |
| 4,882,057 A | * 11/1989 | Morgan et al. | 210/500.28 |
| 4,904,765 A | 2/1990 | Derber et al. | 534/573 |
| 4,918,020 A | 4/1990 | Nowak | 436/56 |
| 4,966,883 A | * 10/1990 | Anderson et al. | 503/208 |
| 5,066,580 A | 11/1991 | Lee | 435/721 |
| 5,145,573 A | 9/1992 | Riedel et al. | 208/14 |
| 5,156,653 A | 10/1992 | Friswell et al. | 44/328 |
| 5,205,840 A | 4/1993 | Friswell et al. | 44/428 |
| 5,250,081 A | 10/1993 | Habeeb et al. | 44/422 |
| 5,252,106 A | 10/1993 | Hallisy | 44/3.28 |
| 5,266,227 A | 11/1993 | Reichelt et al. | 44/328 |
| 5,304,493 A | 4/1994 | Nowak | 436/56 |
| 5,487,770 A | 1/1996 | Dyllick-Brenzinger et al. | 44/328 |
| 5,498,808 A | 3/1996 | Smith | 585/3 |
| 5,558,808 A | 9/1996 | Smith et al. | 508/556 |
| 5,672,182 A | * 9/1997 | Smith | 44/349 |
| 5,676,708 A | 10/1997 | Smith | 8/521 |
| 5,858,930 A | 1/1999 | Desai et al. | 508/261 |
| 5,882,358 A | 3/1999 | Smith et al. | 8/527 |
| 5,939,468 A | * 8/1999 | Siddiqui | 523/161 |

FOREIGN PATENT DOCUMENTS

| | | |
|---|---|---|
| DE | 1643464 | 5/1971 |
| DE | 4308634 A1 | 9/1994 |
| EP | 0 543 057 A1 | 5/1993 |
| FR | 2 141 667 | 1/1973 |
| GB | 361310 | 12/1931 |
| GB | 357179 | 12/1934 |
| JP | 56005227 A * | 1/1956 |
| JP | 54 49198 | 9/1977 |

OTHER PUBLICATIONS

Sekine et al. "4,4',4"–tris(benzoyloxy)trityl as a new type of base–labile group for protection of primary hydroxyl groups", J. Org. Chem. ,1983, 48(18), pp. 3011–3014.*

Patel et al. "Synthesis and thermal study of some unsaturated polyester resins", Acta Cienc. Indica Chem, 1994, 20 (1), pp. 8–10 (Abstract).*

Purr, "A simplfied method for synthesizing phenolphthaline dibutyrate", Naturwissenschaften, 1956, 43, p. 497 (Abstract).*

Dyllick–Brenzinger, et al., "Detection of Marked Hydrocarbon Oils and Azo Dyes Therefor" Chem. Abst. vol. 123 No. 85994 (1995).

* cited by examiner

Primary Examiner—Jill Warden
Assistant Examiner—Yelena Gakh
(74) Attorney, Agent, or Firm—John N. Coulby; Jamie M. Larmann; Collier Shannon Scott, PLLC

(57) ABSTRACT

A compound represented by formula I is used as a marker for organic products,

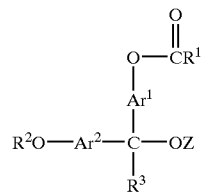

I wherein $Ar^1$ and $Ar^2$ each independently represent a substituted or unsubstituted phenylene group or a substituted or unsubstituted naphthylene group; $R^1$ represents a straight or branched chain alkyl group having 1 to 22 carbon atoms; $R^2$ represents a hydrogen atom or a group of the formula $C(O)R^4$ where $R^4$ is a hydrogen atom or a straight or branched chain alkyl group having 1 to 22 carbon atoms; and $R^3$ represents a hydrogen atom, a straight or branched chain alkyl group having 1 to 12 carbon atoms, a straight or branched chain alkoxy group having 1 to 12 carbon atoms, a hydroxyl group, or a substituted or unsubstituted phenyl group or a substituted or unsubstituted naphthyl group; and Z represents a hydrogen atom or a group of atoms that combine with $Ar^2$ or $R^3$ to form a lactone ring.

9 Claims, No Drawings

AROMATIC ESTERS FOR MARKING OR TAGGING PETROLEUM PRODUCTS

BACKGROUND OF THE INVENTION

1. Field of the Invention

The present invention relates to colorless or essentially colorless compounds useful for marking or tagging various products such as petroleum fuels or solvents and to compositions and methods associated therewith.

2. Description of the Related Arts

A marker is a substance which can be used to tag products, typically petroleum products, for subsequent detection. The marker is normally dissolved in a liquid to be identified, then subsequently detected by performing a simple physical or chemical test on the tagged liquid. Markers are sometimes used by the government to ensure that the appropriate tax has been paid on particular grades of fuel. Oil companies also mark their products to help identify those who have diluted or altered their products. These companies often go to great expense to make sure their branded petroleum products meet certain specifications regarding volatility and octane number, for example, as well as to provide their petroleum products with effective additive packages containing detergents and other components. Consumers rely upon the product names and quality designations to assure that the product being purchased is the quality desired.

It is possible for unscrupulous gasoline dealers to increase profits by selling an inferior product at the price consumers are willing to pay for a high quality branded or designated product. Higher profits can also be made simply by diluting the branded product with an inferior product. Policing dealers who substitute one product for another or blend branded products with inferior products is difficult in the case of gasoline because the blended products will qualitatively display the presence of each component in the branded products. The key ingredients of the branded products are generally present in such low levels that quantitative analysis to detect dilution with an inferior product is very difficult, time consuming and expensive.

Marker systems for fuels and other petroleum products have been suggested but various drawbacks have existed which have hindered their effectiveness. Many, for instance, lose their color over time, making them too difficult to detect after storage. In addition, reagents used to develop the color of markers often are difficult to handle or present disposal problems. Furthermore, some marking agents partition into water. This causes the markers to lose effectiveness when storage occurs in tanks that contain some water, especially alkaline water with a pH up to 10. Some pre-existing markers add color to the petroleum products they mark, which undesirably indicates their presence in the petroleum product, and in some cases violates government regulation by obscuring the colors of other additives.

In view of the above, it would be desirable to provide a compound useful as a marker and that exhibits high solubility in or compatibility with organic-based products, especially petroleum products. Additionally, the marker should have an increased resistance to undesired extraction or removal such as by unscrupulous distributors/retailers. The markers should also appear significantly less intensely colored when undeveloped than many pre-existing marker substances, and thus impart no visual color to the fuels they mark.

SUMMARY OF THE INVENTION

The present invention relates to compounds represented by formula I:

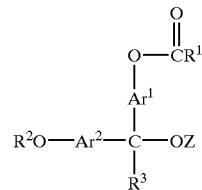

wherein $Ar^1$ and $Ar^2$ each independently represent a substituted or unsubstituted phenylene group or a substituted or unsubstituted naphthylene group; $R^1$ represents a straight or branched chain alkyl group having 1 to 22 carbon atoms; $R^2$ represents a hydrogen atom or a group of the formula $C(O)R^4$ where $R^4$ is a hydrogen atom or a straight or branched chain alkyl group having 1 to 22 carbon atoms; $R^3$ represents a hydrogen atom, a straight or branched chain alkyl group having 1 to 12 carbon atoms, a straight or branched chain alkoxy group having 1 to 12 carbon atoms, a hydroxyl group, a substituted or unsubstituted phenyl group or a substituted or unsubstituted naphthyl group; and Z represents a hydrogen atom or a group of atoms that combine with $Ar^2$ or $R^3$ to form a lactone ring. It further relates to a solution containing one or more of these compounds dissolved in a solvent.

Another aspect of the present invention relates to the use of the compounds of formula I in forming a marked composition. The marked composition comprises an organic product such as a petroleum product or a an organic solvent and a detectable amount of a marker comprised of at least one of the compounds of formula I. These marked compositions can be identified by adding a developing reagent to a sample thereof which forms color in or changes the color of the sample. In one embodiment, a petroleum product can be identified by adding a developing agent and subsequently extracting the developed marker in an extraction medium.

The present invention is based on the discovery that the ester-containing compounds of formula (I) can serve as markers that are colorless or essentially colorless in organic products including liquid petroleum products, provide a distinctive color when reacted with a developing reagent, have good solubility and compatibility with organic products including liquid petroleum products, and are difficult to extract from the marked product in the undeveloped state. The reagents used to develop the color are themselves typically easy to handle and dispose. The colors produced may be chosen to be easily visible against the background color of the fuel and to be easily quantifiable by absorption spectrophotometry.

DETAILED DESCRIPTION OF THE INVENTION

The present invention relates to the compounds of formula I.

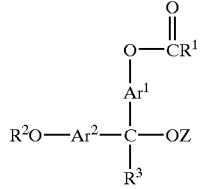

Ar$^1$ and Ar$^2$ each independently represent a substituted or unsubstituted phenylene group or a substituted or unsubstituted naphthylene group. As used herein, a substitutent means any group that is attachable to the phenyl or naphthyl ring that does not ionize or otherwise undergo chemical reaction in the presence of a basic aqueous solution having a pH of 7–13. Typically the substituents include alkyl, halogen, hydroxyl, alkoxy, cyano, carboxylic acid and esters thereof. The OC(O)R$^1$ moiety on Ar$^1$ is preferably in the 4-position in view of the ease in making the compounds and the color and intensity produced. R$^1$ represents a straight or branched chain alkyl group containing 1 to 22 carbon atoms, typically 1–12 carbon atoms, and preferably 1 to 8 carbon atoms. Examples of alkyl groups include methyl, ethyl, n-propyl, i-propyl, n-butyl, i-butyl, sec-butyl, n-pentyl and isomers thereof, but it is not limited thereto.

The OR$^2$ moiety is preferably in the 4-position or 2-position, and more preferably in the 4-position. R$^2$ represents a hydrogen atom or, preferably, a group of the formula C(O)R$^4$ where R$^4$ is a hydrogen atom or a straight or branched chain alkyl group having 1 to 22 carbon atoms, typically 1–12 carbon atoms, and preferably having 1–8 carbon atoms. Such di-ester compounds exhibit superior solubility and stability in organic media such as petroleum products compared with their unesterified counterparts. They also show good color forming properties as will be discussed in more detail below. The alkyl groups R$^1$ and R$^4$ may be the same or different but typically are the same based on the ease and simplicity of the corresponding synthesis. The esters are also much more resistant to inadvertent removal from the petroleum product than their unesterified counterparts.

R$^3$ represents a hydrogen atom, a straight or branched chain alkyl group containing 1 to 12 carbon atoms, more typically 1 to 8 carbon atoms, a straight or branched chain alkoxy group having 1 to 12 carbon atoms, a hydroxyl group, or a substituted or unsubstituted phenyl or naphthyl group. Examples of the alkyl group include methyl, ethyl, n-propyl, i-propyl, n-butyl, i-butyl, sec-butyl, n-pentyl and isomers thereof, but it is not limited thereto. The substituents for the substituted phenyl and naphthyl groups are as defined above and include alkyl, halogen, hydroxyl, alkoxy, cyano, carboxylic acids and esters thereof.

Z represents a hydrogen atom or, more preferably, a group of atoms that combined with Ar$^2$ or R$^3$ forms a lactone ring. For example, a precursor to the lactone ring form has Z as a hydrogen and R$^3$ as a phenyl or naphthyl group having a carboxylic acid group in the 2-position. Normally this compound will readily or instantaneously cyclize the carboxylic acid with the OH to form a five-membered lactone ring (with water being released in the process). In this scenario, Z has been converted, so to speak, from a hydrogen atom to a group of atoms completing the lactone ring.

Preferred compounds of the present invention are represented by formulas II–V.

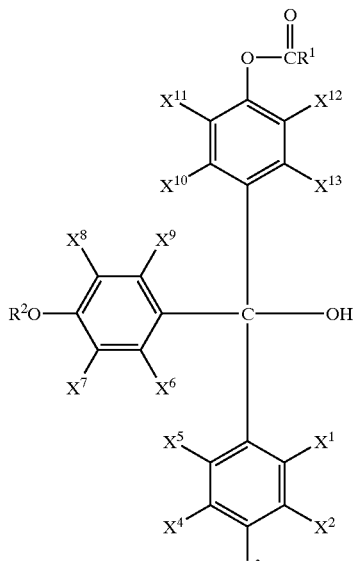

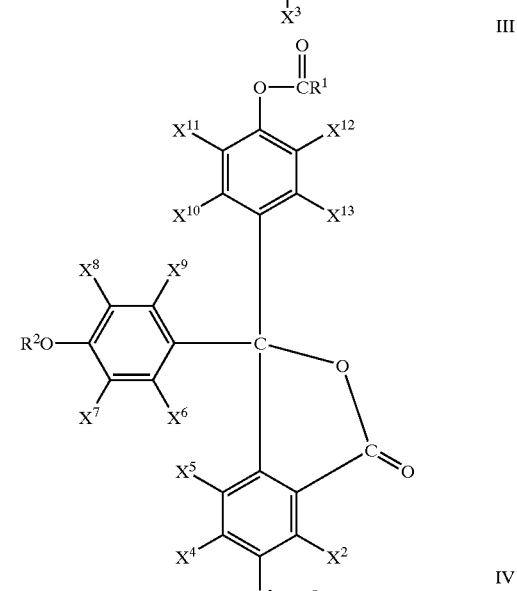

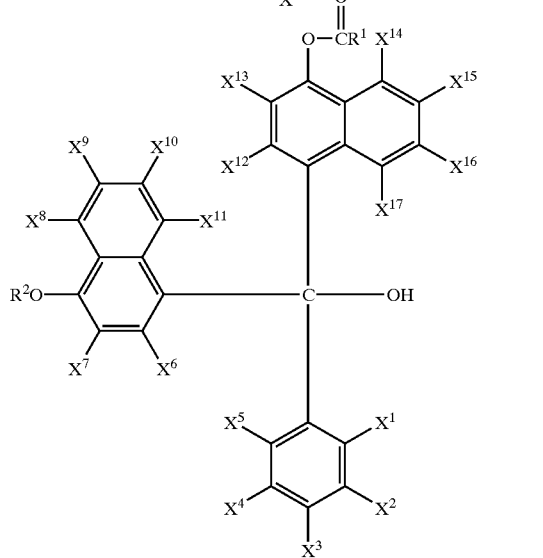

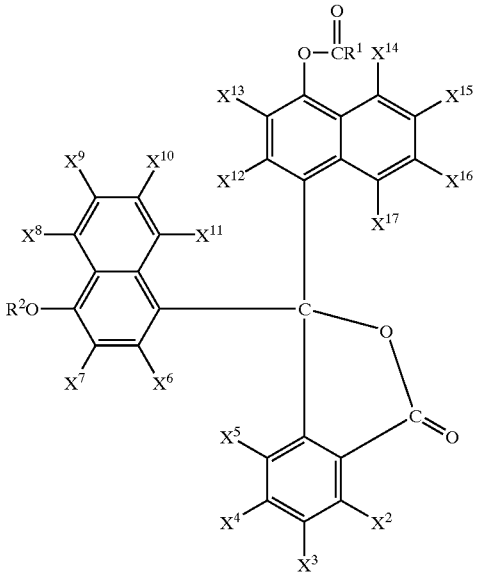

V $R^1$ and $R^2$ have the same meaning as set forth above and $X^1$ represents a hydrogen atom or more preferably a carboxylic acid group. $X^2$–$X^{17}$ independently represent a hydrogen atom, a halogen atom, an alkyl group having 1 to 6 carbon atoms, an alkoxy group having 1 to 6 carbon atoms, a hydroxyl group, a cyano group, a carboxylic acid group, and a carboxylic acid ester group. Preferably, $X^2$–$X^{17}$ are selected from a hydrogen atom, a halogen atom, an alkyl group having 1–6 carbon atoms, more particularly methyl or ethyl, and a carboxylic acid ester having 1–12 carbon atoms, more preferably 1–8 carbon atoms. It is especially preferred that $X^7$ and $X^{11}$ on compounds represented by formulas II and III are not hydrogen atoms, but are instead one of the other substituents recited. When the compounds are intended to mark fuels and thus be combusted, then halogen substituents are generally avoided due to environmental concerns and emission requirements. It should be understood that when $X^1$ is a carboxylic acid group, the above formulas II and III can be thought of as being in equilibrium with one another as follows:

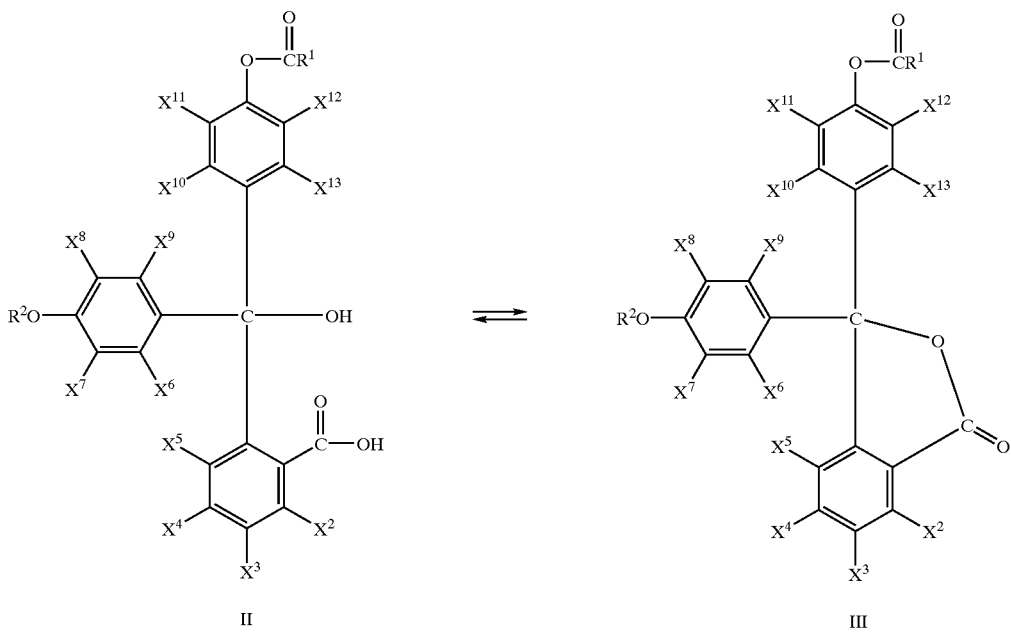

II      III

Correspondingly, the same relationship exits between formula (IV) and formula (V). Under most circumstances, the formation of the lactone forms (III and V) are greatly preferred. The lactones are advantageous in that they increase resistance to inadvertent removal of the markers and minimize the overall color of the undeveloped substances.

The present compounds of formula I are generally colorless or essentially colorless until developed with a developing reagent. Upon development, the compounds of formula I are converted into a colored anion form. For example, it is believed that during development, the ester group $OC(O)R^1$ on $Ar^1$ (or the $OC(O)R^4$ on $Ar^2$, etc.) is hydrolyzed by the developer base and then ionizes to form an oxyanion ($O^-$) group. The presence of such an anion causes the compound to exhibit an intense color. Moreover, by removing the ester moiety and forming a charged ion, the compound becomes much more water soluble. This means that while the compound of formula I is not readily extracted from an organic medium such as a petroleum product, the developed form of compound I is extractable. This allows for removal of the developed compound from the product so as not to cause color interference and/or for a more quantitative analysis of the marker concentration.

Preferred forms of the invention employ a di-ester compound of formula II–V, in part because of the ease and reliability in development. Some of the prior art developable markers required fine control of the kind and amount of developer. For example, some markers are prone to underdevelopment where ion formation is slow or requires more extreme excesses of base to form a color. In some cases over-development may occur with the formation of a double anion which reduces color formation. However, the compounds of formulas IV and V and the compounds of formulas II and III where $X^7$ and $X^{11}$ are not hydrogen atoms, minimize this effect. It is believed that while one ester group is hydrolyzed and ionized to form a powerful electron donor, the other ester group is hydrolyzed and then forms a ketone oxygen atom as an electron acceptor: the oxyanion and the ketone in concert produce the visible color. Further, it is believed that opening and ionization of the lactone group, where present, precedes the hydrolysis of the ester groups and the formation of color.

The compounds of formula I can be used as markers in organic products, typically petroleum products and other organic solvents as a means to identify the petroleum product or solvent by color development. The petroleum products include fuels, lube oils and greases, for example, and the other organic solvents include xylene, toluene, isooctane and methylene chloride, although the invention is not limited thereto. Examples of liquid petroleum products that can be marked by the present invention are gasoline, diesel fuel, fuel oil, kerosene and lamp oil. A preferred petroleum product is diesel fuel, which is composed principally of linear, branched or cyclic alkanes. Any one or combination of the compounds of formula I can thus be used as a product marker. The markers, or compounds, of the present invention may advantageously be used in combination with one another, or with other kinds of markers including fluorescent markers. The use of two or more markers allows for a variety of colors and unique marker compositions to be formulated by simply varying the relative concentrations of each marker. The mixtures with various relative concentrations may thus be marketed and sold as distinct products even when only the relative quantities, and not the identities of the markers used, are varied.

The marker compounds may be added to the petroleum product or solvent in dry form as a powder or crystals or as a liquid solution concentrate. Liquid forms are usually preferred for handling reasons. To provide a liquid concentrate solution containing marker, the marker is dissolved or diluted into at least an equal weight of an organic solvent to create a non-aqueous solution that has a high solubility in petroleum products. Suitable solvents for use with liquid petroleum products include aromatics and aprotic solvents. For instance, aromatic hydrocarbons, including alkyl benzenes such as xylene, and naphthalenes as well as aromatic alcohols, including benzyl alcohol and aromatic substituted alkanols, such as phenolglycolether, are suitable for use. Aprotic solvents include formamide, N,N dimethylformamide, N,N dimethyl acetamide, 1-methyl pyrrollidinone, 1-octyl pyrrolidinone, 1-dodecyl pyrrolidinone, and the like. The 1-octyl pyrrolidinone solvent is a particular preferred aprotic solvent. These solvents may be used singly, or advantageously, in blends. In one embodiment, the blend comprises a mixture of aromatic solvent or solvents with aprotic solvent or solvents in a ratio of organic:aprotic of 99:1 to 1:99 parts by weight, more typically 25:75 to 75:25. When combined with appropriate solvents, markers of the present invention form stable liquid compositions that dissolve readily into petroleum product. The availability of marker compounds to be stable, free-flowing liquids makes them much more attractive to the petroleum industry than dry or solid products primarily because liquids are easier to handle. Dry or solid forms of markers can, however, be used directly.

For example, a liquid concentrate solution may be generally comprised of about 5–50% by weight marker in an organic solvent. Preferable ranges for the solution are 10–50%, more typically 10–35%, and usually from 15–25% marker, based on the total weight of all markers. As stated above, suitable solvents include both aprotic solvents as well as mixtures thereof. The amount of aprotic solvents included in the solution depends upon the amount of marker added, the chemical structure of the marker, the viscosity of the solution, the relative cost of the aprotic solvent used, as well as other factors known in the art. The aromatic solvent or cosolvents used in a particular liquid concentrate solution will be selected based upon the type of petroleum product that is to be marked. For instance, a more volatile solvent will be chosen to mark gasoline products and a less volatile solvent will be used in liquid concentrate solutions used to mark and identify diesel or home heating oil products.

A typical liquid concentrate comprises 10 to 35% of a marker compound of formula I, 0 to 40% of an aprotic solvent and the balance of an aromatic solvent. In one embodiment, the liquid concentrate comprises 15 to 25% of a marker compound of formula I, 20–40% of an aprotic solvent, and 45 to 65% of an aromatic solvent.

The marker is added to an organic product to be marked or tagged in a detectable amount. A "detectable amount" of the marker is an amount that allows for detection of the developed marker by visual observation, spectroscopic instrumentation, or liquid chromatography either in the marked organic product or in an aqueous extraction medium. Spectrophotometer scans, generally in the visible range, may be interpreted in the regular absorbance/transmittance modes. But, where there is significant solvent background color, the results are preferably interpreted by the second derivative mode or method. Typically, the amount of marker present in an organic product ranges from at least about 0.05 ppm to 50 ppm, more commonly from 0.1 ppm to 10 ppm and most preferably at a level of about 0.5 ppm to about 5 ppm.

Because the markers are colorless or essentially colorless and soluble in organic products, their presence is detected by reacting them with a developer or developing reagent. For use in the present invention, the developing reagent is an electron donating compound such as a base, preferably a strong base such as an alkali metal hydroxide, or most preferably a quaternary alkyl ammonium hydroxide. The developing reagent is generally added to a sample of the marked product so as to form a concentration of at least 10 ppm, more typically 100 to 1000 ppm, and more typically about 200 to about 600 ppm. The presence of base reactable substances such as acids in the marked product can compete for the developer reagent and thereby require more developer reagent to be added.

The developer reagent is preferably dissolved in a solvent that is miscible with the marked sample to form a developer composition. Typically, the developer comprises 1%–10%, more preferably 2%–5%, by weight, of the developing reagent. The volume ratio of developer added to a sample is preferably between 1/1000 and 1/2, and more preferably is between 1/20 and 1/5. The developer composition may further comprise a buffering agent in order to assist in controlling the development conditions and specifically to suppress over-development.

After addition of the developer reagent, the sample is inspected to determine whether the developed marker is present therein. This inspection can be visually carried out with the unaided eye or with appropriate instrumentation such as ultraviolet, visible or infrared absorption spectrophotometers or liquid chromatography. The determination may be qualitative or quantitative, the latter allowing for the detection of dilution of the marked product. Furthermore, because the markers of the present invention form watersoluble anions upon reaction with the developing reagent, the markers can be concentrated into an aqueous extraction medium.

Provided that only a qualitative indication of the presence of the marker is required, the now colored, "developed," fuel sample may be returned to its source. In this way, the developing reagent and marker are burned or used up with the product so that no potentially hazardous waste from, say, a roadside test, accumulates for disposal. Prior to returning the marker-developed fuel sample to its original source, the marker may be rendered colorless once again by the addition of a fuel miscible acid, preferably an organic carboxylic acid such as oleic or iso stearic acid. In this way fuel at the original source will not be color contaminated by the addition of "developed" fuel which may contain active, unreacted developer.

Alternatively, the colored marker may be rendered more visible by extraction from the developed fuel sample into an extraction medium. This may be accomplished by addition of water alone as an extraction medium to the sample, but the use of mixtures of water and a phase separation enhancer such as aliphatic alcohols, glycols, or glycol ethers are preferred. Use of a phase separation enhancer promotes an easier separation of the aqueous and organic phases. Typically the extraction medium is added to the petroleum sample in a ratio of about 1% to about 20% by volume. Additionally, other substances, for example pH buffer salts, may be present in the extractant phase to stabilize the colored anion or marker. In one embodiment, the extraction medium further comprises a developing reagent such as quaternary alkyl ammonium hydroxide compounds to provide a one step method for developing and extracting the marker. Other strong bases, of course, may be used, particularly alkali metal hydroxides. The use of extraction is preferred when the color of the developed marker is obscured by other coloring agents in the petroleum product or when the concentration is low.

The compounds of formula I can be made by reaction schemes generally known within the art starting from known or commercially available starting materials. In general, a di- or tri-aryl carbinol (or lactone) having at least one hydroxy group on an aryl group is subjected to an esterification reaction to form the ester compounds of the present invention. The formation of the compounds of formula I is not limited thereto and other ways for forming the same will be readily apparent to the worker of ordinary skill in the art.

The following examples serve to illustrate but do not limit the scope of the invention.

EXAMPLE 1

346 grams o-cresolphthalein are suspended in 1500 mls xylene contained in a stirred reaction flask fitted with condenser. 190 grams of butyric anhydride is added, followed by 2 grams of methane sulfonic acid as a catalyst. The mixture is then brought to a reflux and held until the o-cresolphthalein is completely converted to its di butyrate ester, as can be determined by infrared spectroscopy or by chromatography. The contents are then placed under vacuum and heated to 150° C. to remove all readily volatile material from the system This includes the solvent xylene, unreacted butyric anhydride, and butyric acid formed as a consequence of the butyration.

The non-volatile contents of the flask consisting essentially of the dibutyl ester of the o-cresolphthalein are now mixed with two times their own weight of 1 octyl 2 pyrrolidinone, then diluted further with Aromatic® 200 solvent (Aromatic® is a registered trademark of Exxon Corporation), to produce a 20% solution of the ester. This composition has extended resistance to crystallization even at –35° C.

EXAMPLE 2

A 2 liter glass flask fitted with stirrer, thermometer and heating mantel has charged to it 100 grams methane sulfonic acid, 120 grams of o-cresol and 90 grams of phthalic anhydride. The mixture is stirred and heated to 100° C. where it is maintained for about 20 hours, until a process test shows that the maximum yield of product has been obtained. The reaction mixture is then poured into 800 grams of ice and water mixture. The mixture is then alkalized with 120 grams of sodium hydroxide 50% solution to a pH of 9–10 while maintaining the temperature below 50° C. by applying cooling as necessary. A suspension of o-cresolphthalein results and the product may be filtered, washed and dried. It is then ready to convert to, for example, the di-n-butyrate ester by using the procedure detailed in Example 1.

Alternatively, instead of recovering the o-cresolphthalein by filtration, a water immiscible solvent may be added to the aqueous suspension of the substance, for instance 200 grams of Aromatic® 200. The system now has added to it 80 grams of sodium carbonate and 40 grams of sodium hydroxide. The o-cresolphthalein mostly dissolves to form a deep purple solution whose temperature is adjusted to 35° C. 210 grams of n-butyric anhydride is added slowly while the temperature is held below 50° C. The experiment is then stirred until formation of the di-n-butyrate ester is complete, as may be determined by thin layer chromatography. 500 grams of water is now added and the reaction mixture heated to 90° C. before transfer to a separating funnel. After a period of settlement the mixture separates into two phases. The lower aqueous phase is removed and discarded. The upper organic phase containing the product is then dried free from water by the application of heat, preferably under a vacuum. The dried composition is then standardized to product content of 20%, after which it is filtered to remove any suspended insoluble material. This filtered concentrate has good freeze/thaw stability down to –10° C. It is fully miscible with gasolines.

A 10 milligram per liter solution of the above concentrate in K-1 kerosene can be reacted with a base developer to produce a clear bluish red color with a wavelength of maximum absorption at around 573 nm.

EXAMPLE 3

A reaction is carried out as in Example 2 except that about 60% by weight of the total Aromatic® 200 is replaced by 1 octyl pyrollidinone. This concentrate has excellent resistance to crystallization even down to −35° C. In contrast to the concentrate produced in Example 2, this product concentrate is freely miscible with gasoline, diesel fuel and kerosene in all proportions.

EXAMPLE 4

A chemical synthesis as described in Example 3 is carried out, except that the ortho cresol reagent is replaced by an equimolar amount of ortho secondary butyl phenol.

The final concentrate is even more stable than that of Example 3 and is completely soluble even in saturated fuels like commercial kerosene. When developed in fuel it produces a much bluer shade of red than in Example 3, with an absorbance maximum at around 580 nm.

EXAMPLE 5

The synthesis described in Example 3 is repeated with the ortho cresol replaced by its meta isomer. An equally stable ester concentrate is obtained. This product develops to a purple color with maximum absorption around 582 nm.

EXAMPLE 6

1 gram molecular equivalent of 1 naphtholphthalein is suspended in xylene, as in Example 1, and reacted with an excess of technical grade lauric anhydride. When acylation is complete the reaction mixture is standardized to a concentration of 20% active product with octyl pyrrolidinone. The resultant mixture has good storage stability. When developed in kerosene it produces a clear turquoise color with its peak absorbance around 650 nm

EXAMPLE 7

An analogue of 1-naphtholphthalein is made by starting with heptylated 1-naphthol produced by the Friedel-Crafts alkylation of 1-naphthol with commercial grade mixed heptene isomers.

The heptylnaphtholphthalein synthesis proceeds by the method detailed in Example 2 and the product is converted finally to its diacetate ester by reaction with acetic anhydride. The final product is very weakly colored and forms a stable concentrate in an Aromatic® 200/Octyl pyrrolidinone mixture in the ratio of 3:2. Its developed color is clear blue-green with an absorbance maximum at 655 nm.

EXAMPLE 8

The synthesis described in Example 2 is repeated with 167 grams of thymol substituted for the o-cresol. The final developed color is a clear blue with an absorbance amximum around 598 nm.

EXAMPLE 9 o-Cresolphthalein dibutyrate ester as produced in Example 1 is dosed into one liter of diesel fuel at 4 ppm. 100 ml of this marked diesel is placed in a clear glass bottle. To the bottle is added 10 ml of a solution of benzyltrimethylammonium hydroxide (2%) in 2-ethylhexanol. The immediate intense red color confirmed the presence of the marker. The amount of marker present was then determined by placing a small amount of the developed diesel in a standard cuvette and read on a spectrophotometer at its maximum absorbance of 580 nm. By comparing the absorbance to that of the standard of known concentration, the original 4 ppm concentration is confirmed.

EXAMPLE 10

Four milligrams o-cresolphthalein dibutyrate ester is added to one liter of diesel fuel. To mimic fuel fraud, ten milliliters of this solution is then added to 90 ml of unmarked diesel fuel. Ten milliliters of benzyltrimethylammonium hydroxide (2%) in 2-ethylhexanol is then added and the immediate formation of red color confirmed the presence of marker in the sample of fuel. This color is quantified on a spectrophotometer and a concentration of 0.4 ppm marker is determined.

EXAMPLE 10

The same test is performed as in Example 10, but meta-cresolphthalein from Example 5 is substituted for o-cresolphthalein dibutyrate ester. The color of the developed marker is reddish violet.

EXAMPLE 12

One part of a solution, containing 20% thymolphalein dibutryate ester and 80% solvent, is mixed with 8 parts of stove oil. The resultant solution is added to home heating oil at a dosage rate equivalent to 90 ppm. 100 ml of the home heating oil solution is then mixed well with 10 ml of benzyltrimethylammonium hydroxide (2%) in 2-ethylhexanol A blue color confirmed the presence of the marker compound.

EXAMPLE 13

Ten milligrams thymolphalein dibutryate ester is added to one liter of xylene. 100 ml of this solution is placed into a clear glass bottle. Ten milliliters of benzyltrimethylammonium hydroxide (5%) in ethanol is added. The immediate blue color confirmed the presence of the marker compound.

EXAMPLE 14

Ten milliliters of the solution prepared in Example 13 is added to 90 ml of gasoline. Ten milliliters of benzyltrimethylammonium hydroxide (5%) in ethanol is added. The immediate blue color confirmed the presence of the marker compound.

EXAMPLE 15

Two milligrams of the compound made in Example 4 is added to one liter of gasoline. 100 ml of this solution is placed into a clear glass bottle. Ten milliliters of a 5% caustic soda solution is added and the bottle capped and shaken vigorously. A violet-red colored, aqueous, layer separates out at the bottom of the bottle that confirms the presence of the marker compound.

EXAMPLE 16

Eight milligrams of the compound made in Example 6 is added to one liter of gasoline. 50 ml of this solution is placed in a clear glass bottle. One milliliter of a 20% solution of benzyltrimethylammonium hydroxide in methanol is added to the bottle. A small turquoise layer separates out at the bottom of the bottle, confirming the presence of the marker.

EXAMPLE 17

A solution is made and tested as in Example 13, but using the substance described in Example 7 in place of the thymolphthalein dibutryate ester. The developed color is blue-green.

The invention having been thus described, it will be obvious that the same may be modified in many ways without departing from the spirit and scope of the invention as defined in the following claims.

What is claimed is:

1. A method of marking a petroleum product comprising the steps of:

dissolving or diluting a marker compound into an organic solvent selected from the group consisting of aromatic and aprotic solvents to form a concentrate solution, wherein the marker compound is represented by the formula:

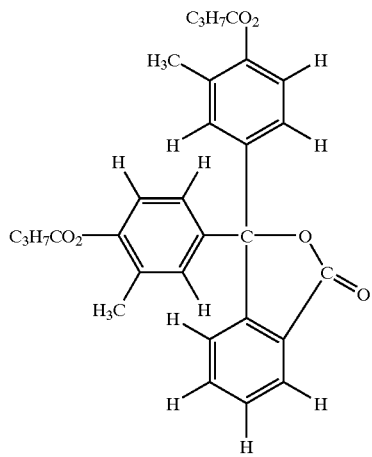

and adding the concentrate solution to the petroleum product.

2. The method according to claim 1, wherein the step of forming a concentrate solution further comprises the step of dissolving or diluting the marker compound into at least an equal weight of the organic solvent.

3. The method according to claim 1, wherein the step of forming a concentrate solution further comprises the step of dissolving or diluting the marker compound to comprise about 5–50% by weight of the marker compound in the organic solvent.

4. The method according to claim 1, wherein the petroleum product is selected from the group consisting of gasoline, diesel fuel, fuel oil, kerosene, and lamp oil.

5. The method according to claim 1, wherein the aromatic solvent is selected from the group consisting of xylene, napthalenes, benzyl alcohol, and phenolglycolether.

6. The method according to claim 1, wherein the aprotic solvent is selected from the group consisting of formamide, N,N dimethylformamide, N,N dimethyl acetamide, 1-methyl pyrrolidinone, n-octyl pyrrolidinone, and 1-dodecyl pyrrolidinone.

7. The method according to claim 1, wherein the organic solvent comprises aromatic and aprotic solvents in a ratio of aromatic:aprotic of 25:75 to 75:25 parts by weight.

8. The method according to claim 1, further comprising the step of adding a developing reagent to the petroleum product to render the marker compound detectable.

9. The method according to claim 8, wherein the developing reagent comprises a quaternary ammonium hydroxide.

* * * * *